United States Patent
Imhauser

(10) Patent No.: US 9,566,022 B2
(45) Date of Patent: Feb. 14, 2017

(54) APPARATUS AND METHOD FOR DETERMINING 3D LOAD DISPLACEMENT RESPONSE OF A JOINT

(71) Applicant: Hospital for Special Surgery, New York, NY (US)

(72) Inventor: Carl Imhauser, South Orange, NJ (US)

(73) Assignee: Hospital for Special Surgery, New York, NY (US)

( * ) Notice: Subject to any disclaimer, the term of this patent is extended or adjusted under 35 U.S.C. 154(b) by 399 days.

(21) Appl. No.: 14/209,538

(22) Filed: Mar. 13, 2014

(65) Prior Publication Data

US 2014/0260701 A1    Sep. 18, 2014

Related U.S. Application Data

(60) Provisional application No. 61/782,640, filed on Mar. 14, 2013.

(51) Int. Cl.
*A61B 5/00* (2006.01)
*A61B 5/11* (2006.01)

(52) U.S. Cl.
CPC ........... *A61B 5/1124* (2013.01); *A61B 5/4528* (2013.01)

(58) Field of Classification Search
None
See application file for complete search history.

(56) References Cited

U.S. PATENT DOCUMENTS

| 4,834,057 | A |   | 5/1989 | McLeod, Jr. |
|-----------|---|---|--------|-------------|
| 5,014,719 | A |   | 5/1991 | McLeod |
| 5,331,851 | A | * | 7/1994 | Parviainen ........... A61B 5/0488 482/133 |
| 5,335,674 | A |   | 8/1994 | Siegler |

FOREIGN PATENT DOCUMENTS

| WO | 88004536 | 6/1988 |
| WO | 9302621 | 2/1993 |

OTHER PUBLICATIONS

Andriacchi, Thomas P. and Dyrby, Chris O., Interactions between kinematics and loading during walking for the normal and ACL deficient knee, Journal of Biomechanics, vol. 38, pp. 293-298, 2005.

(Continued)

*Primary Examiner* — Robert R Raevis
(74) *Attorney, Agent, or Firm* — Kim Winston LLP

(57) ABSTRACT

An apparatus for determining 3D load displacement characteristics of an anatomical joint formed by a first body portion and a second body portion moveable with respect to the first body portion. The apparatus includes a first frame for receiving and securing the first body portion and a load displacement assembly. The load displacement assembly includes a first axis for alignment with a first anatomical plane of the joint, a second frame for receiving and securing the second body portion. The second frame is movable relative to the first frame. The load displacement assembly also includes a first counterweight configured to balance the weight of the second frame, a force for applying a load to the second frame, and a displacement sensor for measuring displacement of the second frame relative to the first frame upon application of the force.

22 Claims, 10 Drawing Sheets

(56) References Cited

OTHER PUBLICATIONS

Andriacchi, Thomas P. et al., A Framework for the in Vivo Pathomechanics of Osteoarthritis at the Knee, Annals of Biomedical Engineering, vol. 32, No. 3, pp. 447-457, Mar. 2004.
Bach Jr., Bernard R. et al., The pivot shift phenomenon: Results and description of a modified clinical test for anterior cruciate ligament insufficiency, The American Journal of Sports Medicine, vol. 16, No. 6, pp. 571-576, 1988.
Bedi, Asheesh et al., A Comparison of the Effect of Central Anatomical Single-Bundle Anterior Cruciate Ligament Reconstruction and Double-Bundle Anterior Cruciate Ligament Reconstruction on Pivot-Shift Kinematics, The American Journal of Sports Medicine, vol. 38, No. 9, pp. 1788-1794, 2010.
Bedi, Asheesh et al., Effect of Tibial Tunnel Position on Stability of the Knee After Anterior Cruciate Ligament Reconstruction: Is the Tibial Tunnel Position Most Important?, The American Journal of Sports Medicine, vol. 39, No. 2, pp. 366-373, 2011.
Shultz, Sandra J., Measurement of Varus-Valgus and Internal-External Rotational Knee Laxities in Vivo—Part I: Assessment of Measurement Reliability and Bilateral Asymmetry, Journal of Orthopaedic Research, pp. 981-988, Aug. 2007.
Brophy, Robert H. et al., Cost Analysis of Converting From Single-Bundle to Double-Bundle Anterior Cruciate Ligament Reconstruction, The American Journal of Sports Medicine, vol. 37, No. 4, pp. 683-687, 2009.
Butler, David L. et al., Location-Dependent Variations in the Material Properties of the Anterior Cruciate Ligament, J. Biomechanics, vol. 25, No. 5, pp. 511-518, 1992.
Conteduca, MD, Fabio et al,. Chondromalacia and chronic anterior instabilities of the knee, The American Journal of Sports Medicine, vol. 19, No. 2, pp. 119-123, 1991.
Daniel, Dale M. et al., Instrumented measurement of anterior knee laxity in patients with acute anterior cruciate ligament disruption, The American Journal of Sports Medicine, vol. 13, No. 6, pp. 401-407, 1985.
Yagi, Masayoshi et al., Biomechanical Analysis of an Anatomic Anterior Cruciate Ligament Reconstruction, The American Journal of Sports Medicine, vol. 30, No. 5, pp. 660-666, 2002.
Denegar, Craig R., and Ball, Donald W., Assessing Reliability and Precision of Measurement: An Introduction to Intraclass Correlation and Standard Error of Measurement, Journal of Sport Rehabilitation, vol. 2, pp. 35-42, 1993.
Edixhoven, PH. et al., Accuracy and Reproducibility of Instrumented Knee-Drawer Tests, Journal of Orthopaedic Research, vol. 5, No. 3, pp. 378-387, 1987.
Emery, Michael et al., Reliability of Force/Displacement Measures in a Clinical Device Designed to Measure Ligamentous Laxity at the Knee, Journal of Orthopaedic and Sports Physical Therapy, pp. 441-447, May 1989.
Fleming, Braden C., Measurement of anterior-posterior knee laxity: a comparison of three techniques, Journal of Orthopaedic Research, vol. 20, pp. 421-426, 2002.
Forster, I.W. et al., Is the KT1000 Knee Ligament Arthrometer Reliable?, The Journal of Bone and Joint Surgery, vol. 71-B, No. 5, pp. 843-847, Nov. 1989.
Greis, MD, Patrick E. et al., Meniscal Injury: I. Basic Science and Evaluation, Journal of the America Academy of Orthopaedic Surgeons, vol. 10, No. 3, pp. 168-176, May/Jun. 2002.
Grood, E.S., and Suntay, W. J., A Joint Coordinate System for the Clinical Description of Three-Dimensional Motions: Application to the Knee, Journal of Biomechanical Engineering, vol. 105, pp. 136-144, May 1983.
Haley, Stephen M., and Fragala-Pinkham, Maria A., Interpreting Change Scores of Tests and Measures Used in Physical Therapy, Physical Therapy, vol. 86, No. 5, pp. 735-743, May 2006.
Hemmerich, A. et al., Measuring three-dimensional knee kinematics under torsional loading, Journal of Biomechanics, vol. 42, pp. 183-186, 2009.
Blankevoort, L. et al., The Envelope of Passive Knee Joint Motion, J. Biomechanics, vol. 21, No. 9, pp. 705-720, 1988.
Mills, O. S. and Hull, M. L., Apparatus to Obtain Rotational Flexibility of the Human Knee Under Moment Loads in Vivo, J. Biomechanics, vol. 24, No. 6, pp. 351-369, 1991.
Mills, O. S. and Hull, M. L., Rotational Flexibility of the Human Knee Due to Varus/Valgus and Axial Moments in Vivo, J. Biomechanics, vol. 24, No. 8, pp. 673-690, 1991.
Imhauser, Carl et al., Abnormal Tibiofemoral Contact Stress and Its Association With Altered Kinematics After Center-Center Anterior Cruciate Ligament Reconstruction, The American Journal of Sports Medicine, vol. XX, No. X, pp. 1-11, 2013.
Imhauser, Carl W. et al., Subject-specific models of the hindfoot reveal a relationship between morphology and passive mechanical properties, Journal of Biomechanics, vol. 41, pp. 1341-1349, 2008.
Isberg, Jonas et al., KT-1000 records smaller side-to-side differences than radiostereometric analysis before and after an ACL reconstruction, Knee Surgery, Sports Traumatology, Arthroscopy, vol. 14, pp. 529-535, 2006.
Jonsson, Hakan et al., Positive pivot shift after ACL reconstruction predicts later osteoarthrosis, Acta Orthop Scand, vol, 75, No. 5, pp. 594-599, 2004.
Kanamori, Akihiro et al., The Forces in the Anterior Cruciate Ligament and Knee Kinematics During a Simulated Pivot Shift Test: A Human Cadaveric Study Using Robotic Technology, Arthroscopy: The Journal of Arthroscopic and Related Surgery, vol. 16, No. 6, pp. 633-639, Sep. 2000.
Kocher, Mininder S. et al., Relationships Between Objective Assessment of Ligament Stability and Subjective Assessment of Syptoms and Function After Anterior Cruciate Ligament Reconstruction, The American Journal of Sports Medicine, vol. 32, No. 3, pp. 629-634, 2004.
Leitze, Zachary et al., Implications of the Pivot Shift in the ACL-Deficient Knee, Clinical Orthopaedics and Related Research, No. 436, pp. 229-236, Jul. 2005.
Lorbach, Olaf et al., A non-invasive device to objectively measure tibial rotation: verification of the device, Knee Surgery, Sports Traumatology, Arthroscopy, vol. 17, pp. 756-762, 2009.
Lorbach, Olaf et al., Reliability testing of a new device to measure tibial rotation, Knee Surgery, Sports Traumatology, Arthroscopy, vol. 17, pp. 920-926, 2009.
Losee, Ronald E., Concepts of the Pivot Shift, Clinical Orthopaedics and Related Research, No. 172, pp. 45-51, Jan.-Feb. 1983.
Lyman, Stephen et al., Epidemiology of Anterior Cruciate Ligament Reconstruction: Trends, Readmissions, and Subsequent Knee Surgery, The Journal of Bone and Joint Surgery, vol. 91-A, No. 10, pp. 2321-2318, Oct. 2009.
Markolf, KL et al., Measurement of knee stiffness and laxity in patients with documented absence of the anterior cruciate ligament, The Journal of Bone and Joint Surgery, vol. 66-A, No. 2, pp. 242-253, Feb. 1984.
Musahl, Volker et al., Development of a simple device for measurement of rotational knee laxity, Knee Surgery, Sports Traumatology, Arthroscopy, vol. 15, pp. 1009-1012, 2007.
Noyes, Frank R. et al., An analysis of the pivot shift phenomenon, The American Journal of Sports Medicine, vol. 19, No. 2, pp. 148-155, 1991.
Lane, Clayton G. et al., In vivo analysis of the pivot shift phenomenon during computer navigated ACL reconstruction, Knee Surgery, Sports Traumatology, Arthroscopy, vol. 16, pp. 487-492, 2008.
Musahl, Volker et al., Effect of Single-Bundle and Double-Bundle Anterior Cruciate Ligament Reconstructions on Pivot-Shift Kinematics in Anterior Cruciate Ligament- and Meniscus-Deficient Knees, The American Journal of Sports Medicine, vol. 39, No. 2, pp. 289-295, 2011.
Ringleb, S. I. et al., The effect of ankle ligament damage and surgical reconstructions on the mechanics of the ankle and subtalar joints revealed by three-dimensional stress MRI, Journal of Orthopaedic Research, vol. 23, pp. 743-749, 2005.
Seon, Jong Keun et al., In Vivo Stability and Clinical Comparison of Anterior Cruciate Ligament Reconstruction Using Low or High

(56) References Cited

OTHER PUBLICATIONS

Femoral Tunnel Positions, The American Journal of Sports Medicine, vol. XX, No. X, pp. 1-7, 2010.
Seon, Jong Keun et al., Comparison of Single- and Double-Bundle Anterior Cruciate Ligament Reconstructions in Restoration of Knee Kinematics and Anterior Cruciate Ligament Forces, The American Journal of Sports Medicine, vol. 38, No. 7, pp. 1359-1367, 2010.
Shino, Konsei et al., Measurement of Anterior Instability of the Knee, The Journal of Bone and Joint Surgery, vol. 69-B, No. 4, pp. 608-613, Aug. 1987.
Siegler, Sorin et al., A Six-Degrees-of-Freedom Instrumented Linkage for Measuring the Flexibility Characteristics of the Ankle Joint Complex, J. Biomechanics, vol. 29, No. 7, pp. 943-947, 1996.
Tandogan, Reha N., Analysis of meniscal and chondral lesions accompanying anterior cruciate ligament tears: relationship with age, time from injury, and level of sport, Knee Surgery, Sports Traumatology, Arthroscopy, vol. 12, pp. 262-270, 2004.
Tashman, Scott et al., Dynamic Function of the ACL-reconstructed Knee during Running, Clinical Orthopaedics and Related Research, No. 454, pp. 66-73, Jan. 2007.
Torzilli, Peter A. et al., Measurement Reproducibility of Two Commercial Knee Test Devices, Journal of Orthopaedic Research, vol. 9, No. 5, pp. 730-737, 1991.
Von Porat, A. et al., High Prevalence of osteoarthritis 14 years after an anterior cruciate ligament tear in male soccer players: a study of radiographic and patient relevant outcomes, Annals of the Rheumatic Diseases, vol. 63, pp. 269-273, 2004.
Wiertsema, S. H. et al., Reliability of the KT1000 arthrometer and the Lachman test in patients with an ACL rupture, The Knee, vol. 15, pp. 107-110, 2008.
Fukuda, Yukihisa et al., A quantitative analysis of valgus torque on the ACL: a human cadaveric study, Journal of Orthopaedic Research, vol. 21, pp. 1107-1112, 2003.
Kanamori, Akihiro et al., The Effect of Axial Tibial Torque on the Function of the Anterior Cruciate Ligament: A Biomechanical Study of a Simulated Pivot Shift Test, Arthroscopy: The Journal of Arthroscopic and Related Surgery, vol. 18, No. 4, pp. 394-398, Apr. 2002.
Wright, Timothy M. and Maher, Suzanne A., Current and Novel Approaches to Treating Chondral Lesions, The Journal of Bone and Joint Surgery, vol. 91-A, Suppl. 1, pp. 120-125, 2009.
Walter, S.D. et al., Sample Size and Optimal Designs for Reliability Studies, Statistics in Medicine, vol. 17, pp. 101-110, 1998.
Imhauser, C. W. et al., ACL Deficiency and Reconstruction Alter Magnitude and Location of Tibiofemoral Contact Stresses, ORS 2011 Annual Meeting, Paper No. 47.
Shindle, Michael K. et al., Magnetic Resonance Imaging of Cartilage in the Athlete: Current Techniques and Spectrum of Disease, The Journal of Bone and Joint Surgery, vol. 88-A, Supp. 4, pp. 27-46, 2006.
Siegler, S. et al., Mechanics of the ankle and subtalar joints revealed through a 3D quasi-static stress MRI technique, Journal of Biomechanics, vol. 38, pp. 567-578, 2005.

\* cited by examiner

APPARATUS AND METHOD FOR DETERMINING 3D LOAD DISPLACEMENT RESPONSE OF A JOINT

CROSS-REFERENCE TO RELATED APPLICATIONS

This application claims the benefit of U.S. Provisional Application No. 61/782,640, filed Mar. 14, 2013, the entire disclosure of which is incorporated by reference herein in its entirety.

BACKGROUND OF THE INVENTION

The present invention relates generally to a measurement device that characterizes the three dimensional (3D) load displacement response of a joint. Specifically, the present invention relates to an apparatus and method for determining load displacement characteristics of an anatomical joint in a clinical or experimental environment, including primary and coupled motions while negating the influence of gravitational forces.

Clinical assessment of joint pathologies, including those involving soft tissues or other ligament injuries, is primarily subjective. The clinician relies on the manual manipulation of the joint. During clinical examination, the clinician obtains a qualitative and subjective "feel" for the amount of laxity or stiffness in the involved joint as compared to the clinician's previous intuition regarding what the normal joint should feel like and/or compared with the contralateral joint should it be uninjured. This clinical examination is then supplemented by the clinical history of the patient and by radiological evaluations. Moreover, assessment of the effectiveness of treatment be it conservative (e.g., rehabilitation) or surgical is subjective and relies on feedback from the patient.

Knee rotations and coupled motions as measured during clinical examination of the knee (pivot shift phenomenon) are an important predictor of clinical outcome and a potential risk factor for osteoarthritis following ligament injuries, such as the ACL. However, conventional knee arthrometers are unidirectional, measuring the translation or rotation only in the direction of the applied force or torque, respectively. They were not designed to characterize knee rotations and coupled motions occurring in response to multiplanar torques, such as what occurs during the pivot shift exam. Therefore, a need remains for a standardized, quantitative, objective, clinically-usable method to assess rotations and coupled motions. Previous devices that measured rotations and coupled motions were cumbersome or relied on complicated, time-consuming methods making them unsuitable for clinical use. Robotic technology has been used extensively in vitro to explore the rotations and coupled motions occurring in response to combined valgus and internal rotation torques, thus simulating the pivot shift exam. Unfortunately, such data has not translated to development of a useful clinical tool. Knee laxity has also been assessed using MR-compatible devices to negate soft tissue artifact; however, the approach is time-consuming and costly, which limits its clinical utility.

Further, conventional arthrometers do not have the capability of balancing each axis of the system resulting in interference with free movement along each axis of the device because the weight of the various segments forming the device act on each axis and generate undesired forces and moments across the anatomical joint due to gravity. Consequently, there is a need for a quantitative, reliable technique to assess the 3D load displacement response of a joint for the purposes of contributing to the clinical management of joint pathologies.

BRIEF SUMMARY OF THE INVENTION

In accordance with a preferred embodiment, the present invention provides an apparatus for determining 3D load displacement response of a joint having a first body segment and a second body segment moveable with respect to the first body segment. The apparatus includes a first frame and a load displacement assembly. The first frame is configured to receive and secure the first body segment. The load displacement assembly includes a first axis, a second frame, a first counterweight, a force and a sensor. The first axis aligns with a first anatomical plane of the joint. The second frame receives and secures the second body segment and is movable relative to the first frame. The first counterweight is configured to balance a weight of the second frame. The force applies a load to the second frame and the sensor measures displacement of the second frame relative to the first frame upon application of the force.

Further, the load displacement assembly of the apparatus includes counterweights configured to balance the forces and moments created/generated by gravity about and along each axis of the apparatus due to the mass of the second frame. The load displacement assembly incorporates/integrates means to apply force and torque to the second frame without interfering with 3D displacements of the second frame relative to the first frame. Furthermore, the apparatus includes measurement of 3D displacements (rotations and translations) of the second frame relative to the first frame and sensors to measure the forces and torques applied about and along each axis of the apparatus.

In accordance with another preferred embodiment, the present invention provides an apparatus for applying loads about multiple axes of a joint without interfering with coupled or primary motions for determining 3D load displacement characteristics of the joint formed by a first body segment and a second body segment moveable with respect to the first body segment. The apparatus includes a first frame for receiving and securing the first body segment. The apparatus further includes a first axis for alignment with a first anatomical plane of the joint, a second axis for alignment with a second anatomical plane of the joint, a third axis for alignment with a third anatomical plane of the joint, a weightless second frame, a first force, a second force, and a first displacement sensor. The weightless second frame receives and secures the second body segment, is movable relative to the first frame, and extends from the first axis. The first force applies a first load to the joint and the second force, which is independent of the first force, applies a second load to the joint. The first displacement sensor measures displacement of the second frame relative to the first frame upon application of at least one of the first and second forces.

In accordance with yet another preferred embodiment, the present invention provides a method of objectively assessing the 3D load displacement response of a joint formed by a first body segment and a second body segment. The method includes the steps of securing the first body segment to a stationary first frame and securing the second body segment to a second frame of a load displacement assembly, wherein the second frame is movable relative to the first frame about a first axis. The method further includes the steps of balancing the weight of the second frame with a counterweight about the first axis, applying a force to the joint, and measuring displacement of the second body segment relative to the first body segment upon application of the force.

In accordance with the present invention, the problems of interfering and coupled motions when assessing the 3D load displacement response of an anatomical joint is solved by engendering an apparatus for determining 3D load displacement characteristics of the joint that measures primary motions (motions in the direction of an applied load) and coupled motions (motions other than in the direction of the applied load), and which is capable of applying loads along and or about multiple axes of the apparatus in isolation or in combination without interfering with coupled motions. Novel aspects of the present invention allow loads to the joint to be applied independently or in combination along any axis of the apparatus. Thus, the apparatus provides a system to independently or simultaneously apply loads along multiple axes of the device without interfering with motions along and about each axis of the device. Further, the apparatus provides a system to offset the effect of gravity on each segment of the device. This prevents the weight of the device (or the forces resulting from the weight of the device) from being transferred across the joint that is being tested. Furthermore, the apparatus provides a novel bearing design that decouples rotations and translations and allows independent locking/unlocking and independent measurement of translations and rotations along and about each axis of the system.

The embodiments of the present invention are based on a novel adoption of theoretical concepts and methodologies to address the lack of quantitative, objective clinical measures of rotations and coupled knee motions in response to multiplanar torques. Further, the embodiments of the present invention are based on adoption of a non-serial instrumented spatial linkage to a joint. Its unique non-serial design enables tracking of the 3D position and orientation of a joint directly in an anatomic coordinate system allowing easy clinical interpretation. A manually-controlled pneumatic actuator system to apply simultaneous multiplanar torques is also applied. Advantages of the present invention include objective, quantitative measures for 3D primary and coupled motions in an anatomical coordinate system that is conducive to easy clinical interpretation.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Figure 1:
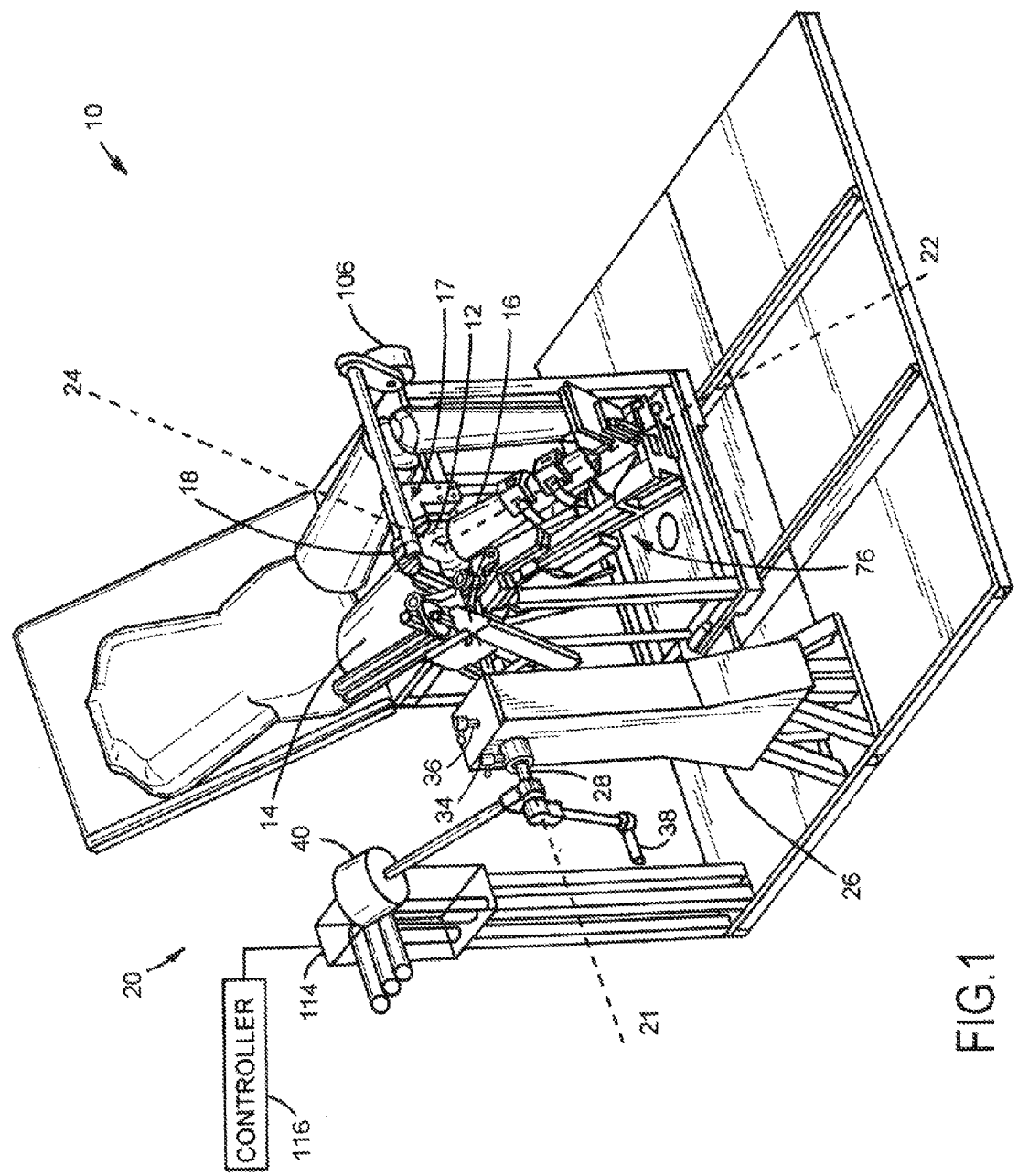
FIG. 1 is a perspective view of an apparatus for determining 3D load displacement characteristics of a joint in accordance with a preferred embodiment of the present invention.

Referring to FIGS. 1-10, in a preferred embodiment, the present invention provides an apparatus 10 for determining 3D load displacement characteristics of an anatomical right knee joint 12 formed by a first body segment 14 and a second body segment 16 movable with respect to the first body segment. The apparatus 10 includes a first frame 17 having a first frame fastener 18 for receiving and securing the first body segment and a load displacement assembly 20. The first frame is rigidly attached to a patient support structure such as a chair and mounted in a fixed position relative to the load displacement assembly. While FIG. 1 illustrates the apparatus as applied to a right knee joint, the apparatus can equally be configured for a left knee joint, such as by a mirrored construction of the apparatus or rotation of the apparatus to accommodate the left knee joint.

The anatomical joint 12 described in connection with the preferred embodiment is a knee joint. The knee joint includes a tibia and a femur, with the femur articulating relative to the tibia or vice versa. The tibia moves relative to the femur in 3D including six degrees of freedom, three translations (medial/lateral, anterior/posterior, proximal/distal) and three rotations (flexion/extension, varus/valgus, internal/external). The tibia flexes relative to the femur throughout a full range of motion from hyperextension to excess of about 120° flexion. The tibia also internally and externally rotates relative to the femur as the tibia flexes throughout a range of motion. Moreover the knee joint has a certain degree of laxity such that the tibia can translate in the anterior-posterior direction relative to the femur and flex so as to be in either valgus or varus. However, it is understood by those skilled in the art that the present invention is not limited to any particular anatomical joint and can be applied to any anatomical joint or any mechanical joint i.e., two objects joined or united, either rigidly or in such as way as to permit motion. For instance, the present invention is equally applicable to the ankle, wrist, elbow, hip, shoulder and any other joint of the human body.

Moreover, the present invention is not limited to body joints with any particular number of pivot axes. For example, the body joint could have one or two pivot axes without departing from the spirit and scope of the invention. Moreover, it is understood by those skilled in the art that the present invention is equally applicable to non-human body joints, such as the knee joint of a monkey or ape, a prosthetic joint or a mechanical joint.

Referring to FIG. 1, the load displacement assembly 20 includes a first axis 21 for alignment with a first anatomical plane of the joint, a second axis 22 for alignment with a second anatomical plane of the joint, a third axis 24 for alignment with a third anatomical plane of the joint, a force for applying a load to the second frame, and a displacement sensor. The force generates a torque to the joint about the second and/or third axes, or a linear force to translate the joint in a direction perpendicular to the first axis. The displacement sensor measures displacement of the second frame relative to the first frame upon application of the force.

The first axis 21 can be aligned e.g., with the epicondyles of the femur, such that when a patient is situated within the apparatus 10 the tibia moves with the second frame, thus allowing the knee joint to flex and extend about the first axis. The second axis 22 is perpendicular to the first axis and is aligned e.g., with the long axis of the tibia such that when the patient flexes and extends the knee, the second axis remains perpendicular to the first axis. The third axis 24 is perpendicular to both the first and second axes i.e., the third axis is floating such that it always maintains perpendicularity with the first and second axes. Specifically, the third axis is perpendicular to the second axis and pivots about the first axis when the patient flexes and extends the knee joint.

Figure 2:
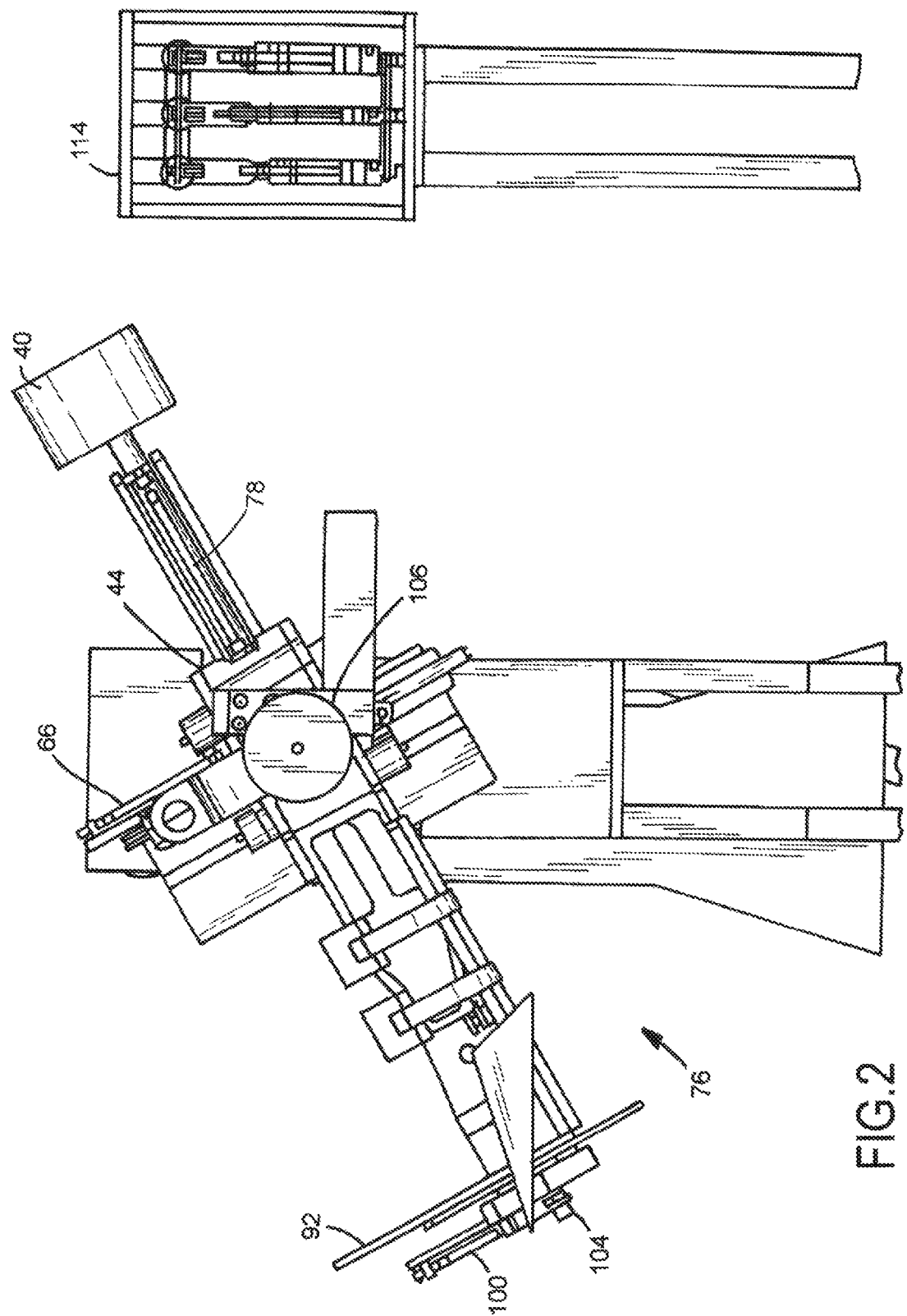
FIG. 2 is a side elevation view of the apparatus of FIG. 1.
Figure 3:
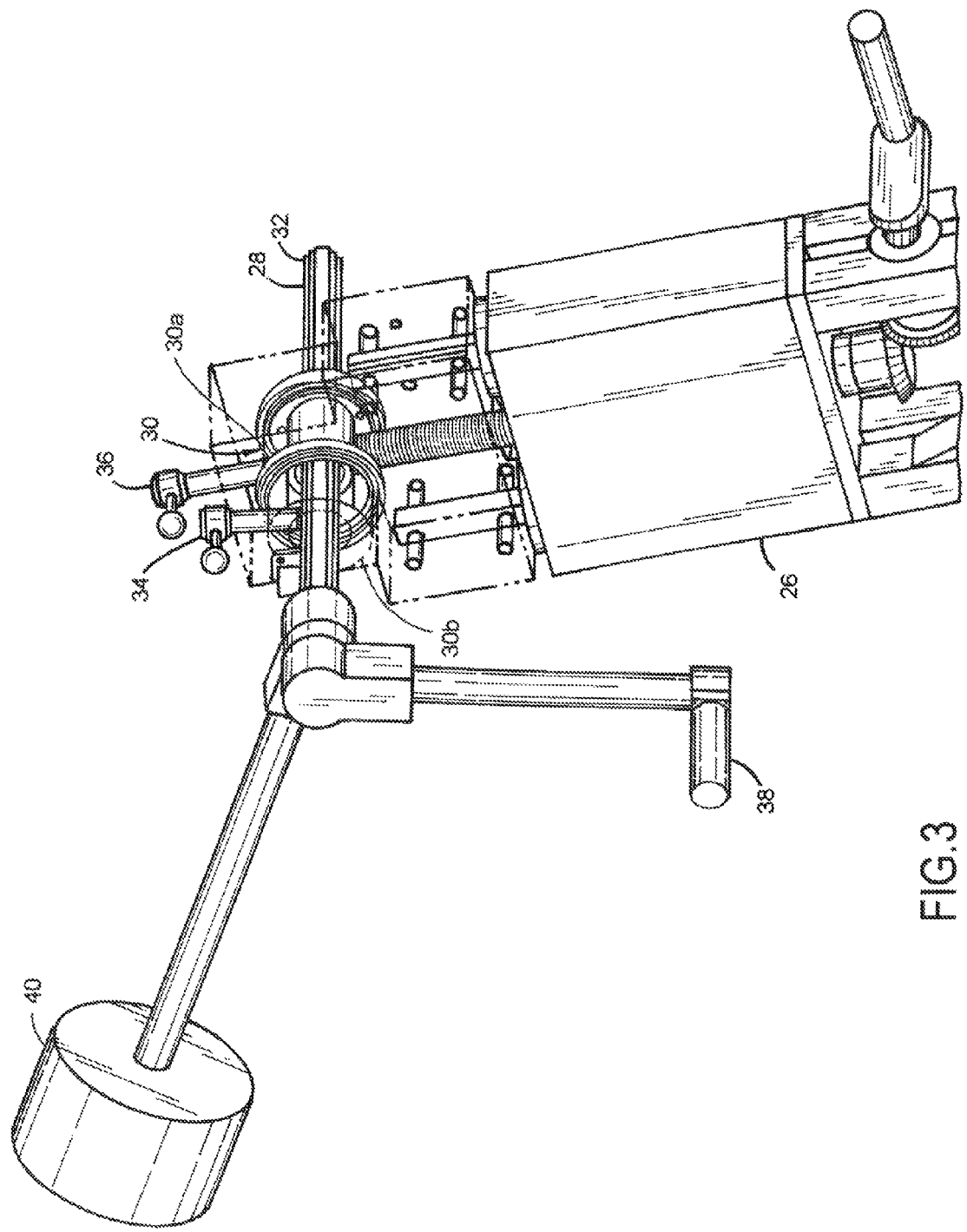
FIG. 3 is an enlarged partial perspective view of a shaft and support of a load displacement assembly of the apparatus of FIG. 1.

Referring to FIGS. 1-3, the load displacement assembly 20 also includes a support 26 about which the entire load displacement assembly is substantially mounted to. Mounted to the support 26 about an upper portion thereof is a shaft 28 that extends along and is coaxial with the first axis. As best shown in FIG. 3, the shaft 28 is supported by and extends through a bearing 30 that circumscribes the shaft. The bearing 30 includes a larger diameter portion 30a and a smaller diameter portion 30b. The support rotatably supports the bearing 30 and a fastener 36 for rigidly fixating the bearing on the support allowing fixation of the second frame at a predefined flexion angle. The shaft 28 is also preferably configured with splines 32 so as to receive another fastener 34 for rigidly fixating the shaft relative to the bearing 30 or for rigidly fixating the bearing 30 along a section of the shaft allowing unconstrained motion along the first axis or fixing translation along the first axis.

Figure 4:
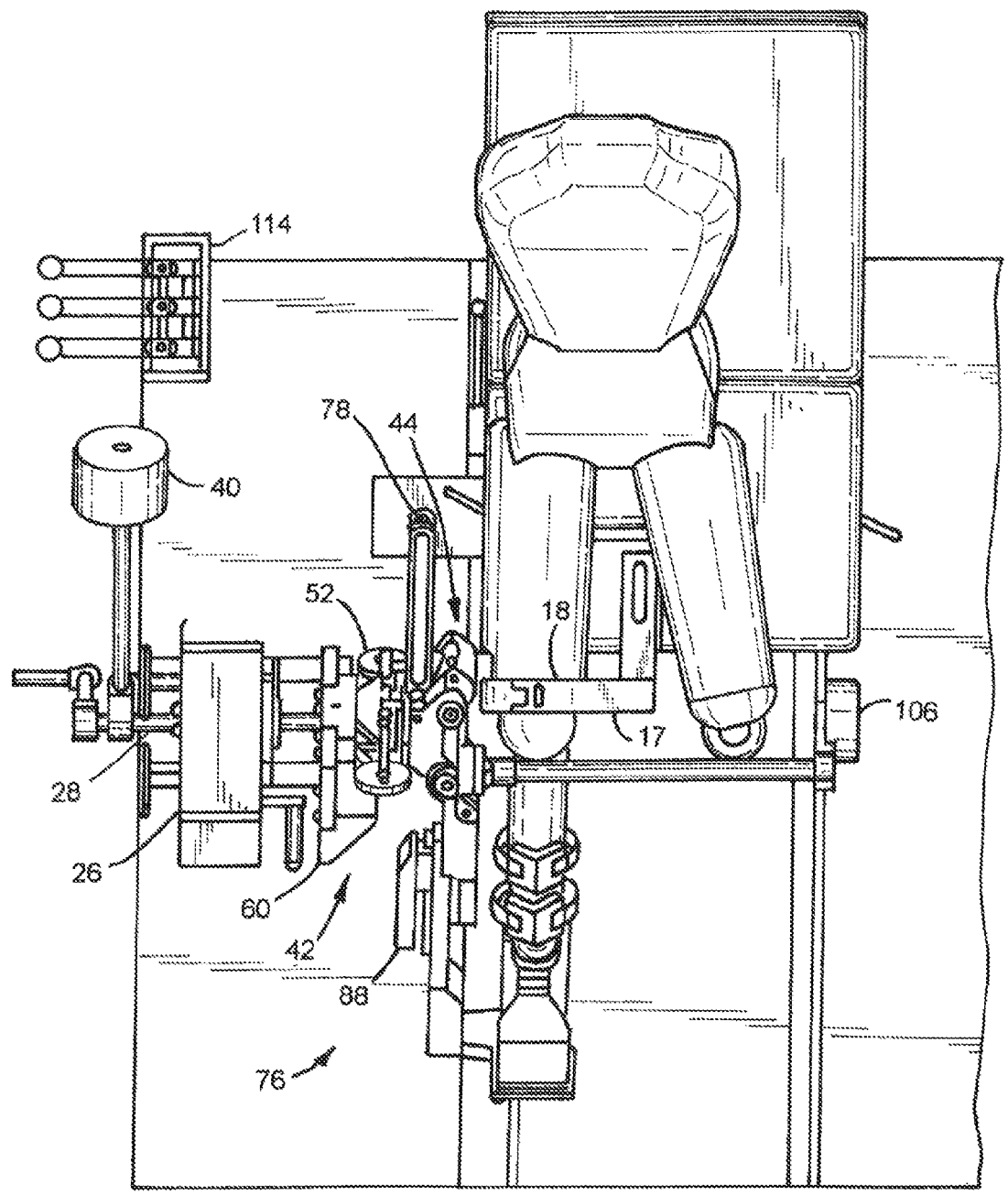
FIG. 4 is a top plan view of the apparatus of FIG. 1.

Referring to FIGS. 3 and 4, the shaft 28 extends through the support 26 such that a portion of the shaft extends beyond a lateral side of the support and a portion of the shaft extends beyond a medial side of the support. About a first end of the shaft that extends beyond the lateral side of the support is crank lever 38 for manually adjusting the rotational position of the shaft about the first axis. Also extending from the first end is a first counterweight 40, as further described below.

Figure 5:
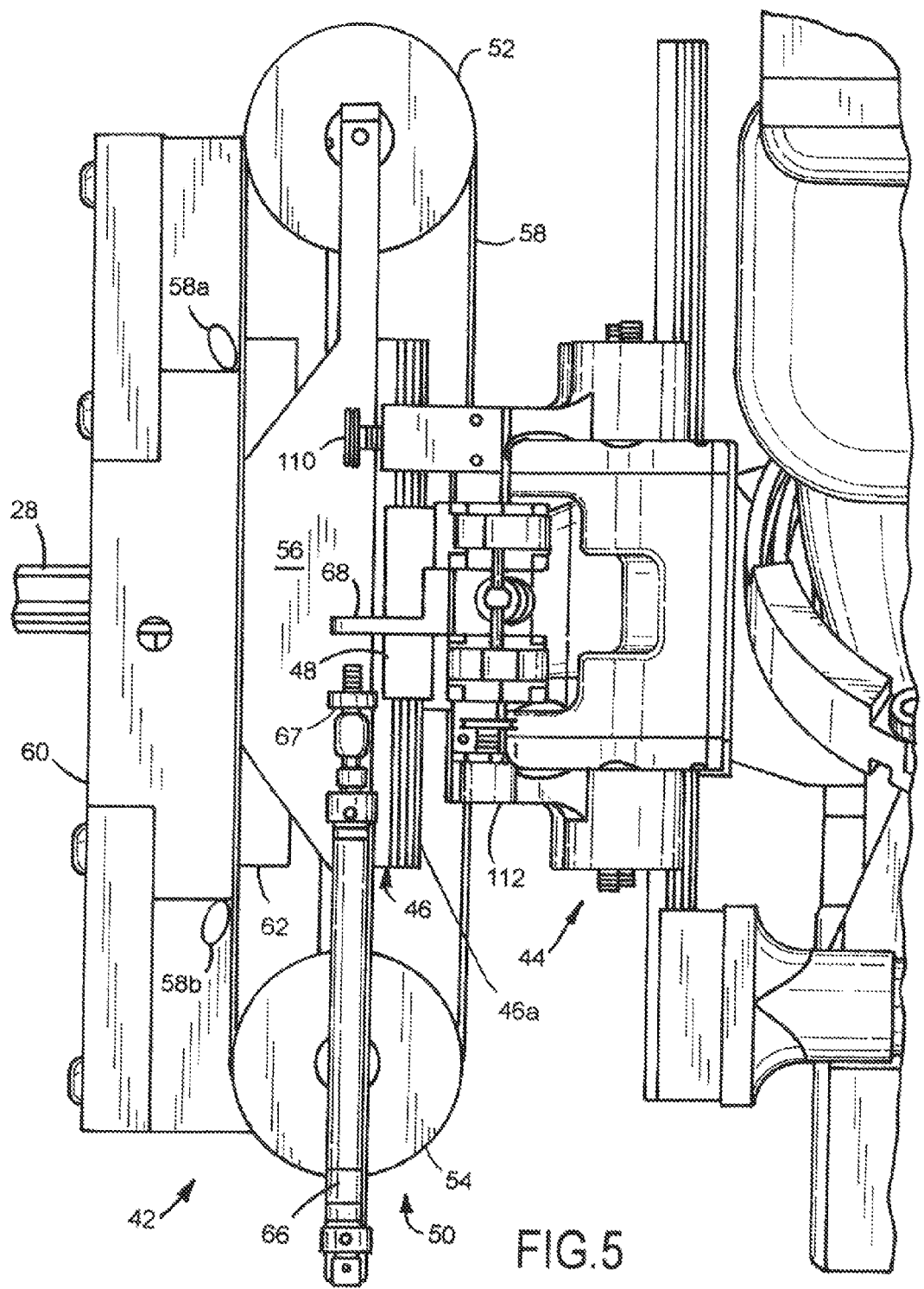
FIG. 5 is an enlarged top plan view of a second counterweight pulley system of the apparatus of FIG. 1.

Connected to the shaft 28 about a second end opposite the first end are a second counterweight assembly 42 and a third axis swivel 44. The second counterweight assembly 42 is positioned between the third axis swivel and the support 26. As best shown in FIG. 5, the second counterweight assembly 42 is rigidly connected to the shaft 28 and the third axis swivel 44 is connected to the counterweight assembly 42 by a linear bearing 46. The linear bearing 46 includes a stationary part 46a rigidly mounted to the shaft 28 extending along the first axis and a moving par 48 i.e., a female track connected to the third axis swivel. The linear bearing 46 extends parallel to the third axis 24. As used herein the term "parallel" includes substantially parallel, while the term "substantially parallel" includes the ordinary meaning of parallel. The second counterweight assembly 42 is fixedly/rigidly attached to the shaft so as not to rotate about the shaft. The female track 48 of the third axis swivel slidingly engaging the stationary part 46a and is free to travel along the linear bearing under the influence of gravity. Additionally, the linear bearing 46 is rendered weightless by one or more of the first, second, third and fourth counterweights, as further described below.

The second counterweight assembly 42 also includes a pulley 50 having first and second sheaves 52, 54 extending from a support 56 and a cable 58. The cable 58 extends between the first and second sheaves and connects with a second counterweight 60. The second counterweight 60 is connected to the support 56 via a linear bearing 62 so as to be slidable relative to the support 56 in a linear direction. The second counterweight 60 is fixed in positioned along a length of the cable 58 by the respective ends 58a, 58b of the cable being secured to opposite ends of the second counterweight. For example, a first end of the cable 58a is secured to one end of the second counterweight and a second end of the cable 58b is secured to an opposite and of the second counterweight. The cable 58 also extends through the third axis swivel 44 and is fixedly attached to the third axis swivel 44, such that the third axis swivel does not slide along the cable.

The pulley 50 is fixedly attached to the shaft 28 so as not to pivot relative to the shaft. However, the second counterweight 60 is configured with a slot 64 (FIG. 6) to allow the second counterweight 60 to freely translate along the length of the slot by way of bearing 62 and balance the weight of load displacement assembly about the first axis. Specifically, the second counterweight 60 translates along an axis parallel to the third axis 24 (via linear bearing 62) and counterbalances the weight of the third axis swivel 44, which translates along the linear bearing 46. In other words, the load displacement assembly includes a second counterweight configured to balance the weight of the load displacement assembly about the first axis and which translates along a path parallel to the third axis.

In operation, the third axis 24 of the load displacement assembly 42 pivots about the first axis 22 as the patient flexes and extends the knee joint. When the knee joint is at approximately 90° flexion, the third axis extends in a substantially horizontal direction. When the third axis extends in the substantially horizontal direction, the second counterweight ceases to provide a counterbalancing force to the third axis swivel 44. However, as the knee joint flexion angle decreases and the third axis 24 moves further away from a substantially horizontal direction the effects of the second counterweight increases and has a maximum effect when the third axis extends in a substantially vertical direction.

Referring back to FIG. 5, the load displacement assembly 20 also includes a cylinder 66 for generating a force to move the third axis swivel 44 in a linear direction along the linear bearing 46. The cylinder has one end fixedly connected to an end of the support 56 and an opposite end connected to a support bracket 68 which is connected to the third axis swivel 44. For purposes of illustrating the present embodiment, the cylinder 66 in FIG. 5 is shown disconnected from the support bracket 68. Thus, operation of the cylinder 66 causes the third axis swivel 44 to translate along the linear bearing 46. In other words, the cylinder 66 provides a force (e.g., a first force) for applying a load to the joint about the third axis 24, such as a force in a direction parallel to the third axis. This is accomplished by the cylinder 66 applying a force to the moving part 48 via support bracket 68 to generate a load on the second frame. A force sensor 67 is attached in series with the cylinder 66 to measure the applied force.

The third axis swivel 44 is configured as best shown in FIGS. 6-9. The third axis swivel 44 is a curved bearing (or rotational bearing) having a stationary part 70 and a moving part 72. The stationary part is mounted to the shaft 28 which extends along the first axis. The curved bearing is configured to have an arc formed by a radius extending out from the third axis 24 whose center forms the location of the third axis 24. The stationary part is slidingly connected to the moving part and travels along a curved track 74 formed on the moving part. However, the curved track 74 can alternatively be formed on the stationary part with cooperating members extending from the moving part. The moving part 72 is also connected to a second frame 76, as further described below. Additionally, the third axis swivel 44, including the curved bearing, is rendered weightless by one or more of the first, second, third and fourth counterweights, as further described below.

The moving part 72 is configured to translate along the curved bearing so as to rotate about the third axis 24. Movement of the moving part 72 causes varus and valgus rotation of the second frame 76 about the third axis. Movement of the moving part 72 relative to the stationary part 70 is effectuated by a cylinder 78 (FIG. 8) that extends along a path parallel to the second axis 22 and applies a force to the moving part to generate a torque about the third axis. The cylinder 78 consequently provides a force (e.g., a second force) for applying a load to the joint about the third axis 24, such as a torque force about the third axis, and includes a force sensor mounted in series for measurement of the applied force. The second force provided by cylinder 78 is independent of any other forces, such as the first force or any other coupled forces acting on the joint.

Figure 6:
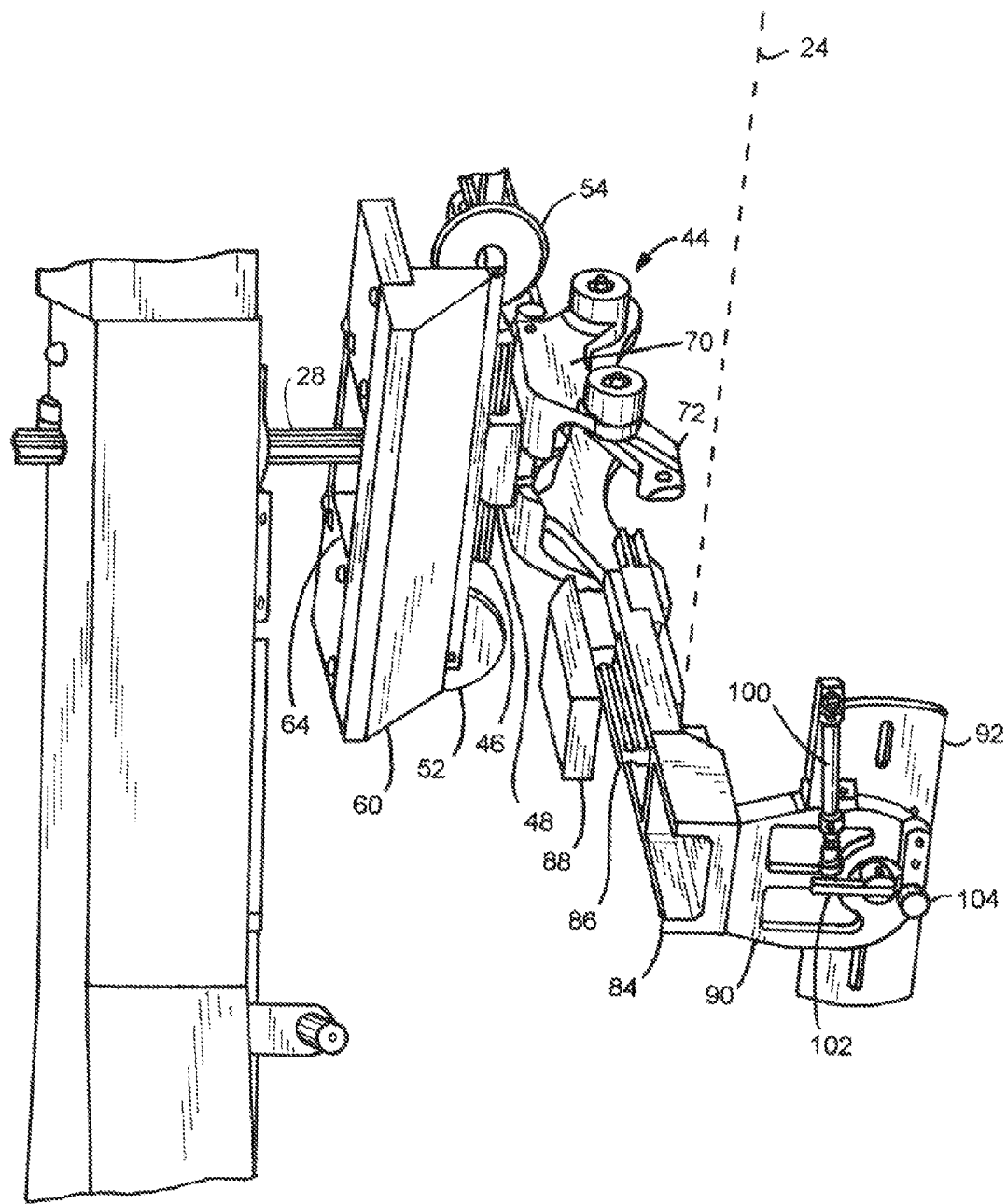
FIG. 6 is a bottom perspective view of a second frame of the apparatus of FIG. 1.
Figure 7:
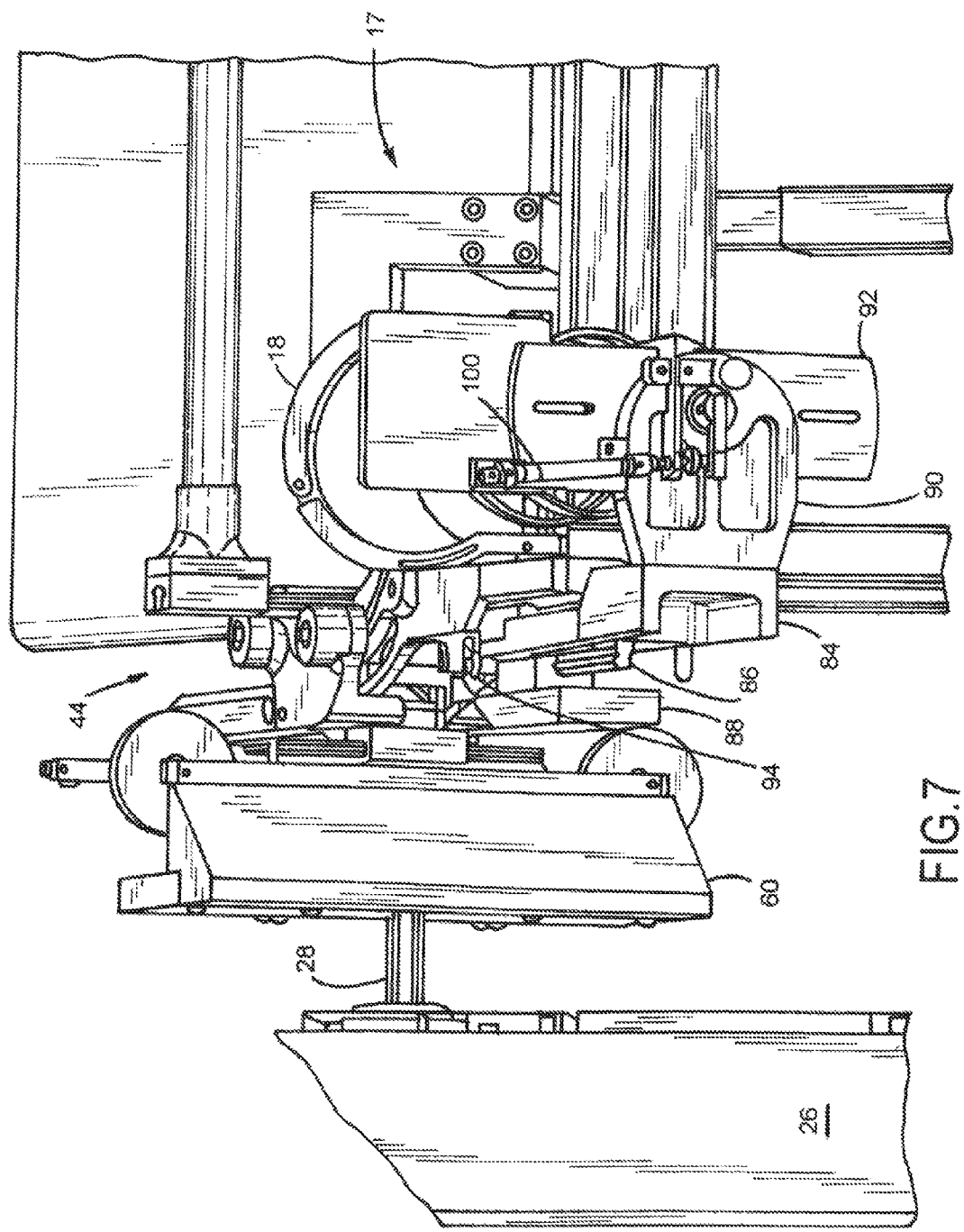
FIG. 7 is another bottom perspective view of a second frame of the apparatus of FIG. 1.
Figure 9:
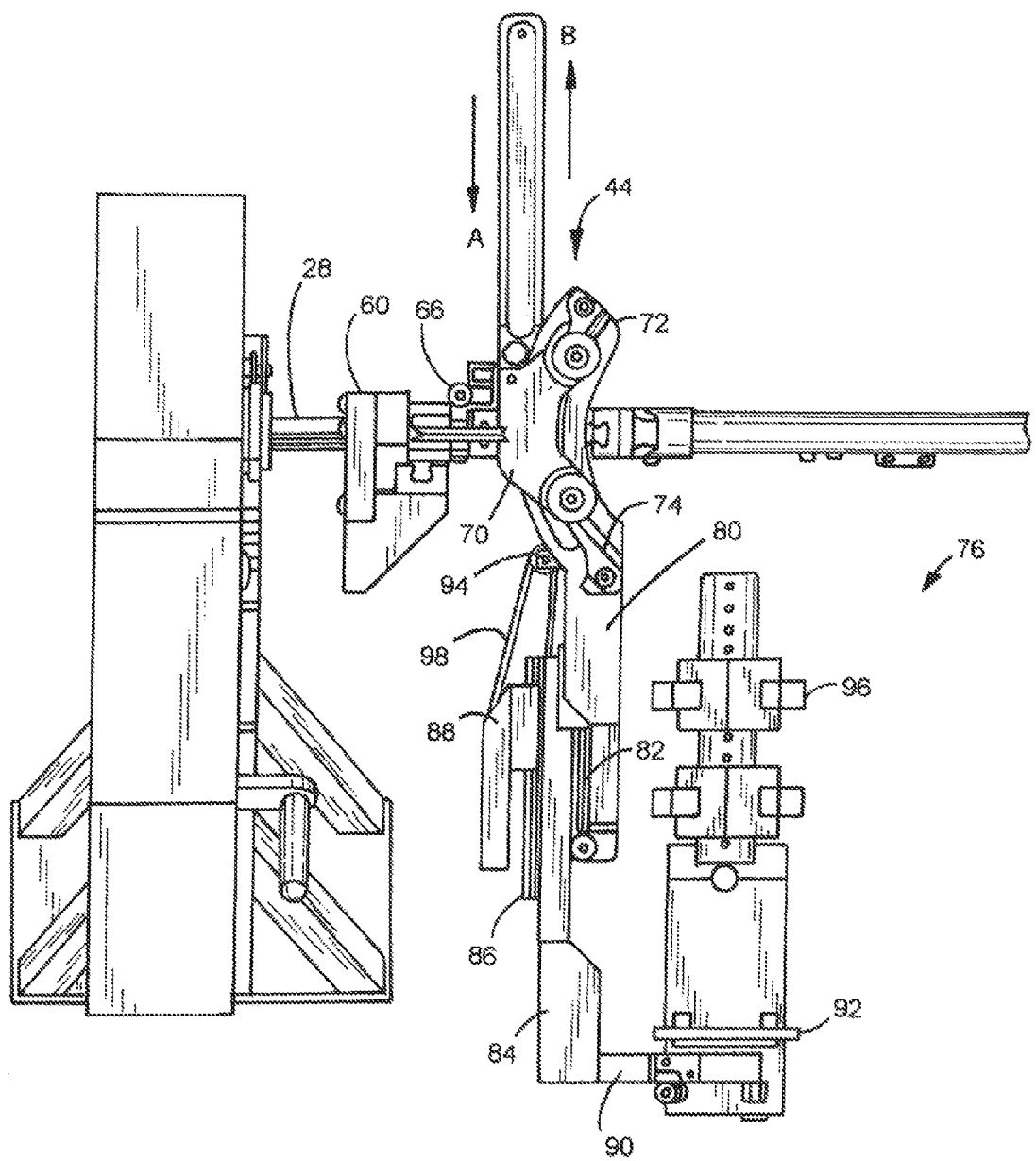
FIG. 9 is an enlarged partial perspective view of the apparatus of FIG. 1.

Referring to FIGS. 1, 6 and 9, the second frame 76 includes a first segment or translator segment 80, a linear bearing 82, a second segment or foot support segment 84, a second linear bearing 86, a third counterweight 88, a foot support mount 90, and footplate 92. The first segment 80 is rigidly attached to the moving part 72 of the third axis swivel 44 and moves correspondingly with the moving part. The first segment 80 extends from the moving part 72 so as to align parallel with the second axis 22. Attached to a lateral side of the first segment is the linear bearing 82 which is aligned to be parallel with the second axis 22. The second segment 84 is connected to the first segment 80 via the linear bearing 82 such that second segment 84 translates along the linear bearing. The linear bearing 82 is positioned about a medial side of the second segment and the second linear bearing 86 is positioned about a lateral side of the second segment. The second linear bearing 86 is aligned to be parallel with the second axis 22 and the linear bearing 82. Slidingly engaged with the second linear bearing 86 is the third counterweight 88, which translates along the second linear bearing and is supported by a pulley 94, as further described below.

The foot support mount 90 is connected to a distal end of the second segment 84 extending in a medial direction for supporting the footplate 92. The footplate 92 is pivotably mounted to the foot support mount and configured to receive and support a foot of the patient. Extending upwardly from the foot plate 92 and foot support mount 90 is a second frame fastener 96 for attaching to and fastening the tibia of the patient to the second frame 76.

Referring to FIG. 9, the first segment 80 also includes the pulley 94 which extends outwardly from its lateral side. The pulley 94 has a cable 98 with one end connected to the third counterweight 88 and an opposite end connected to the second segment 84. The third counterweight 88 is configured to balance the weight of the load displacement assembly and translate along a path parallel to the second axis 22. Specifically, the third counterweight balances the weight of the second segment about the pulley 94 and prevents the second segment from sliding off of the linear bearing 82. Thus in operation, the second segment can be adjusted to various extended positions relative to the first segment while the third counterweight balances the weight of the second segment and its associated components such as the foot support mount, foot plate and second frame fastener. Further, as the third counterweight and pulley 94 operate along a path parallel to the second axis 22, the third counterweight has no effect when the patient extends the knee joint to full extension such that the second frame 76 is substantially horizontal. However, the effect of the third counterweight increases as the patient flexes the knee joint and has a maximum effect when the patient flexes to about 90° flexion such that the second frame is substantially vertically oriented.

Referring to FIG. 6, the load displacement assembly 20 also includes a cylinder 100 that applies a force (e.g., a third force) to the joint about the second axis 22. The cylinder 100 can also include a force sensor mounted in series for measuring the applied force supplied by the cylinder. As used herein, a force about an axis includes a force in a direction parallel to the axis and/or a force perpendicular to the axis for generating a torque force about the axis. The cylinder 100 has a fixed or stationary end attached to an extension of the foot support mount 90 and an opposite end attached to a lever 102. The lever arm 102 has one end attached to the cylinder and an opposite end rigidly attached to a shaft connected to the footplate 92. Thus, operation of the cylinder 100 applies a torque force to the joint via the lever arm which rotates the foot plate about the second axis.

Adjacent the lever arm 102 is a potentiometer 104 for measuring the angular displacement of the second frame 76 relative to the first frame 17 upon application of the torque force to the footplate 92. The displacement of the second frame relative to the first frame is indicative of the load displacement response of the joint.

Referring back to FIG. 1, the second frame 76 is configured as a weightless second frame. The second frame is made weightless by the first counterweight 40. That is, the weight of the second frame 76 is balanced by the first counterweight 40. Specifically, as the second frame extends from the shaft 28, the torque force about the shaft generated by the weight of the second frame is offset by the weight of the first counterweight 40 which extends from the shaft 28. In other words, the second frame extends from the first axis and the first counterweight balances the weight of the second frame about the first axis. Thus, when a patient is situated within the load displacement assembly, the patient will not be subject to the weight of the second frame exerted on his tibia, thus eliminating any forces and resulting motions exerted on the joint by the weight of the load displacement assembly.

Figure 10:
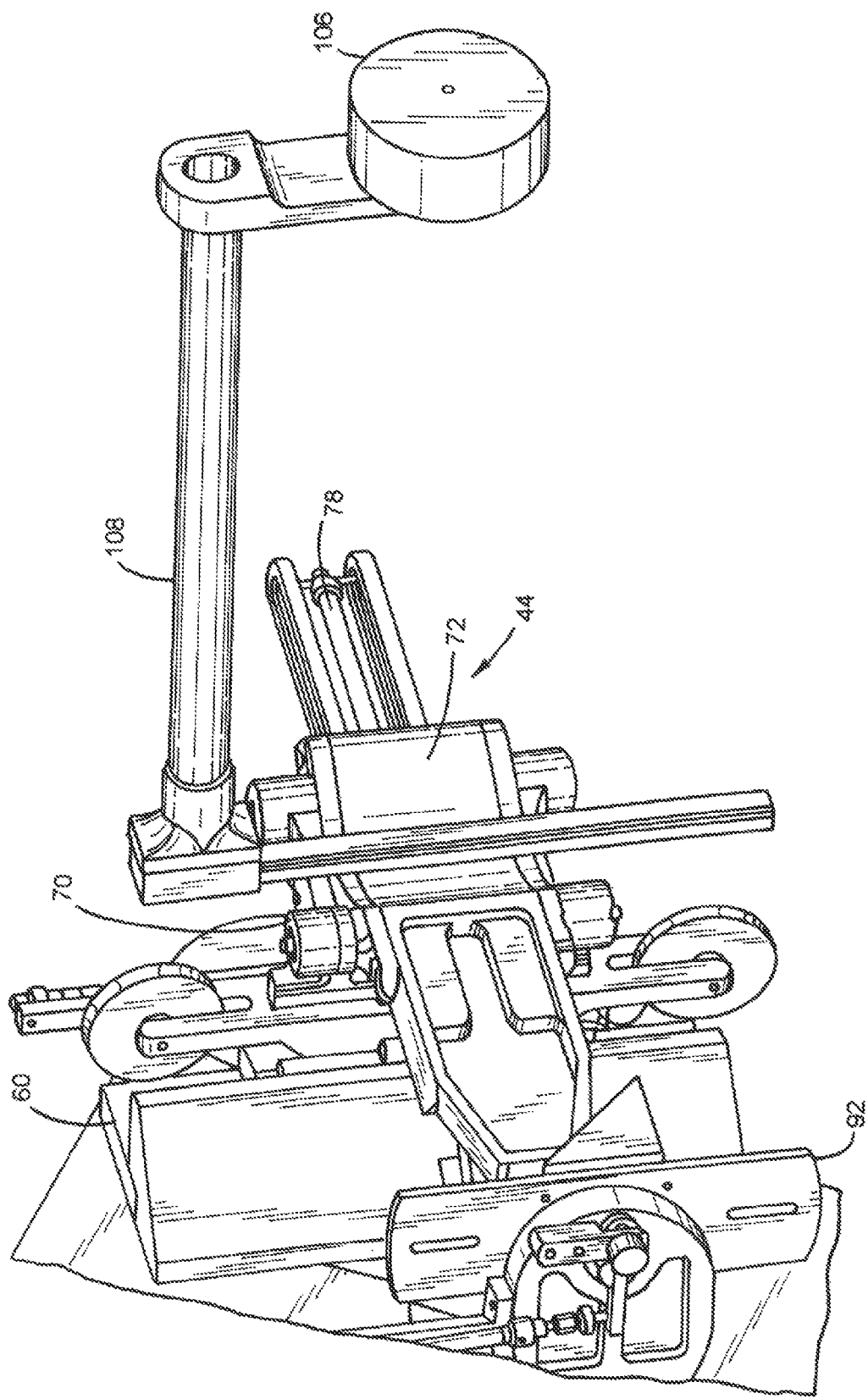
FIG. 10 is an enlarged partial perspective view of a fourth counterweight attached to the apparatus of FIG. 1.

Referring to FIGS. 1 and 10, the load displacement assembly 20 also includes a fourth counterweight 106 that is connected to and extends from the third axis swivel 44. The fourth counterweight is connected to the third axis swivel 44 by a linkage 108 that extends along a path parallel to the shaft 28. The fourth counterweight balances the weight of the load displacement assembly about the third axis 24. Specifically, the fourth counterweight balances the weight of the various components of the load displacement assembly about an opposite side of the third axis 24. More particularly, when the second frame 76 is positioned substantially horizontally, the fourth counterweight has no effect on the load displacement assembly. However, when the patient flexes the joint to move the joint from full extension to flexion, the second frame pivots from the horizontal position and the effect of the fourth counterweight increases and has a maximum effect when the patient flexes to about 90° flexion such that the second frame is substantially vertically oriented.

Figure 8:
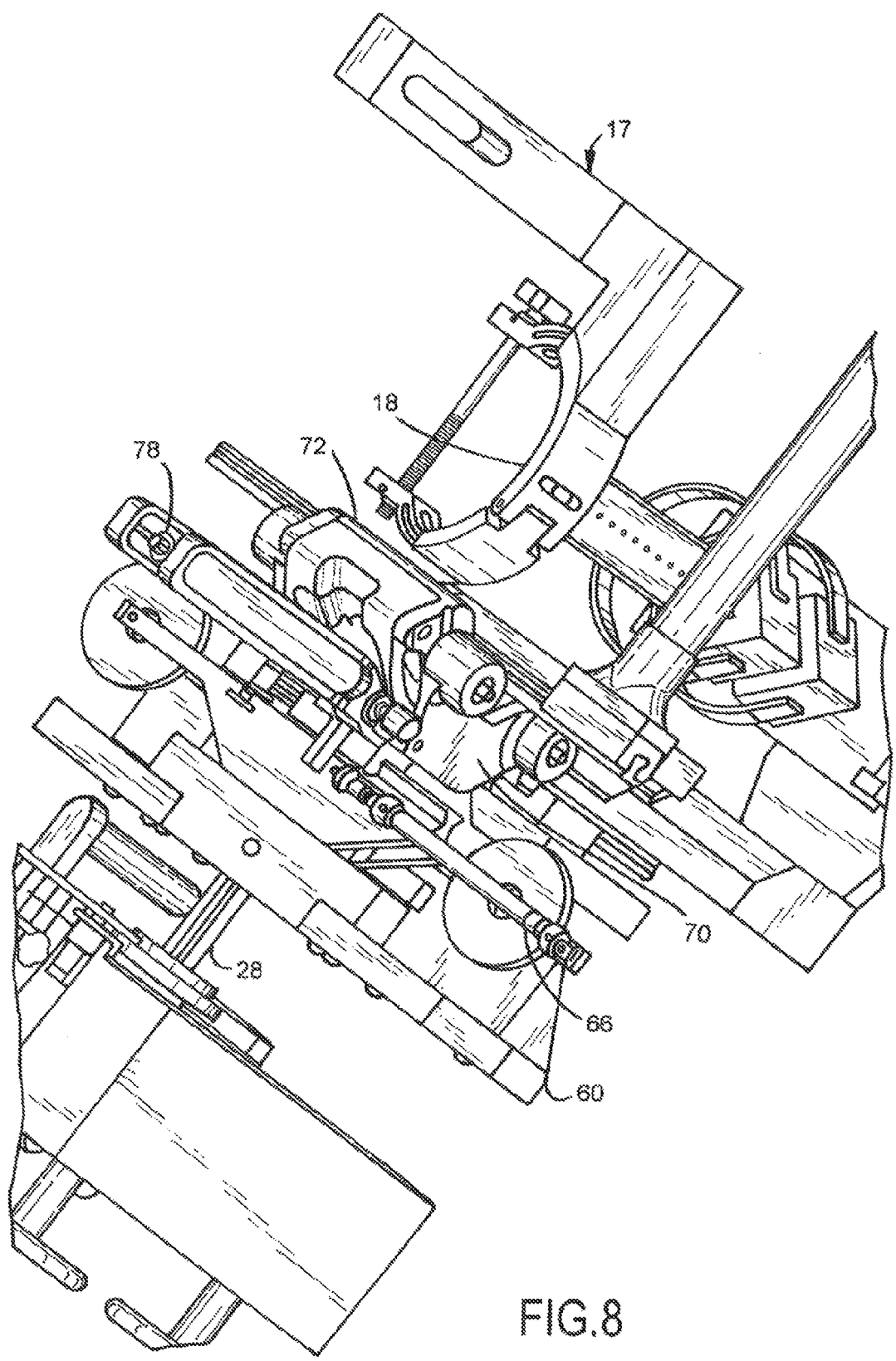
FIG. 8 is an enlarged partial top perspective view of the apparatus of FIG. 1.

Referring back to FIG. 5, the load displacement assembly includes a linear potentiometer 110 (i.e., a first displacement sensor) for measuring linear displacement of the joint upon application of a force, such as a force supplied by the cylinder 66. More specifically, the potentiometer 110 measures linear displacement of the second frame 76 (which is secured to the second body segment) upon application of a force supplied by the cylinder 66. Additionally, the load displacement assembly includes an angular potentiometer 112 (i.e., a second displacement sensor) for measuring angular displacement of the joint upon application of a force supplied by the cylinder 78 (FIG. 8). More specifically, the angular potentiometer 112 measures angular displacement of the second frame 76 upon application of force supplied by the cylinder 78, so as to measure e.g., the knee joint in varus/valgus.

Referring back to FIG. 1, the apparatus 10 also includes a pneumatic control station 114 which includes a plurality of pneumatic controls operatively connected to the various cylinders of the load displacement assembly 20. Preferably, the pneumatic control station is configured with individual pneumatic controls for controlling specific cylinders of the load displacement assembly. Each individual pneumatic control can be configured to supply a predetermined pressure to a cylinder such that the cylinder provides a predetermined force to the joint.

The apparatus 10 also includes a controller 116, such as a computer, microprocessor, or pneumatic switch controller that is operatively connected to each of the pneumatic control station 114, cylinders 66, 78, 100, potentiometer's 104, 110, 112 for applying forces/loads to the joint and measuring displacement of the joint upon application of a load, and sensors for measuring amount of force and displacement which are recorded and visualized on the controller e.g., via data acquisition. Applicable microprocessors, sensors, and potentiometers applicable to the present embodiment are also disclosed in U.S. Pat. No. 5,335,674, the entire disclosure of which is hereby incorporated by reference. The controller can also include an emergency stop controlled by the patient which vents all pneumatic pressure within the apparatus thus preventing transmission of force to the load displacement assembly.

In an exemplary operation and as best illustrated with reference to FIG. 1, a patient is seated within a chair with his right leg secured to the chair by the first frame 17. The first frame fastener 18 then clamps onto a distal femur portion of the patient for securely fastening the leg in a stationary position. With the distal femur secured in position, the knee joint is free to flex throughout a full range of motion.

The patient's tibia is then secured to the second frame 76 and clamped to the second frame via second frame fasteners 96 (FIG. 9). To adjust for variations in the length of a patient's tibia, the second segment 86 is free to move to an extended position to accommodate tibias of varying length. In other words, the overall length of the second frame can be adjusted to accommodate the length of any individual tibia. With the patient's tibia and femur fully secured to the apparatus, the patient's leg is then free to move about a full range of motion.

Moreover, once a patient's leg is mounted to the apparatus 10, no external forces are applied to the knee joint as a result of the apparatus itself owing to the weightless nature of the various components of the load displacement assembly. That is, the weight of the second frame 76 will not impose any forces on the knee joint since the weight of the second frame is balanced by one or more counterweights. For example, the amount of weight or size of the first counterweight 40 can be adjusted to accommodate legs of different mass and/or lengths.

To then evaluate the 3D load displacement response of the knee joint, a load or first force is applied to the joint and displacement of the joint measured by a first displacement sensor upon application of the first force. For example, to measure the amount of anterior-posterior laxity of the knee joint when at 90° flexion, a predetermined force in the anterior-posterior direction is applied to the joint by cylinder 66 (FIG. 5). With the cylinder 66 rigidly connected to the shaft 28, operation of the cylinder applies a first force to the third axis swivel 44 via support bracket 68 and consequently the second frame 76 in the anterior-posterior direction. Then the amount of linear displacement of the tibia relative to the femur is measured with the linear potentiometer 110 (i.e., a first displacement sensor). Specifically, the amount of linear displacement of the second frame 76 relative to the first frame 17 is measured. Thus, as the first and second frames are securely fastened to the femur and tibia respectively, the amount of linear displacement of the second frame relative to the first frame is indicative of the amount of linear anterior-posterior displacement of the knee joint.

To assess joint laxity in the varus and valgus direction, the patient's leg e.g., can be extended at full extension or at 90° flexion. Once the leg is positioned, a predetermined force in the varus and valgus direction is applied to the joint by cylinder 78 (FIG. 10). Specifically, cylinder 78 applies a second force to the moving part 72 of the third axis swivel 44 to move the moving part in either a clockwise or counterclockwise direction about the third axis 24. Referring to FIG. 9, if the cylinder 78 applies a force in the direction of arrow A, the load displacement assembly applies a force on the knee joint to move the joint in varus. That is, the force in the direction of arrow A moves the moving part in a counterclockwise direction about the third axis 24, when viewed as in FIG. 9. Alternatively, if the cylinder 78 applies a force in the direction of arrow B, the load displacement assembly applies a force on the knee joint to move the joint in valgus. That is, the force in the direction of arrow B moves the moving part in a clockwise direction about the third axis 24, when viewed as in FIG. 9. Then the amount of angular displacement of the tibia relative to the femur is measured with the angular potentiometer 112 (FIG. 5) i.e., a second displacement sensor which measures the amount of angular displacement of the second frame 76 relative to the first frame 17 upon application of the second force.

To assess the load displacement response of the knee joint with respect to the amount of internal and external rotation of the tibia relative to the femur, a force is applied to the joint via cylinder 100 (FIG. 6), with the knee joint at a predetermined flexion angle. The cylinder 100 applies a torque force to the joint via footplate 92 and the amount of angular displacement of the joint is measured with angular potentiometer 104 which measures the amount of angular displacement of the footplate relative to the first frame 17.

While assessment of the joint can be accomplished with independent forces acting on the joint free of other counterforces, first and second forces can alternatively be applied to the joint simultaneously while first and second displacement sensors measure displacement simultaneously. Additionally, a third force (such as that provided by cylinder 100) independent of the first and second forces can be applied to the joint either independently of the first and second forces or simultaneously with the first and second forces.

In sum, the apparatus 10 comprises three axes that are aligned with the three anatomical planes of a joint. Thus, the applied loads and the resulting six degrees of freedom (DOF) motions have a clinically meaningful interpretation. Loads to the joint are applied through the apparatus to the knee joint by an operator using actuators. Loads are measured using displacement sensors embedded in these actuators/cylinders. Each axis of the apparatus is instrumented with sensors to measure the six DOF motions. Continuous load and displacement data are recorded to a computer and visualized with custom software.

The present invention also provides a method of objectively assessing the 3D load displacement response of an anatomical joint formed by a first body segment and a second body segment. The method includes the steps of securing the first body segment (e.g., a femur or thigh) to a stationary first frame, such as the first frame 17 described the above embodiment. Then the second body segment (e.g., a tibia) is secured to a second frame of a load displacement assembly, such as the second frame 76 of the load displacement assembly 20 described in the above embodiment. The second frame is movable relative to the first frame about a first axis, such as a first axis aligned with a first anatomical plane of the joint. For example, with respect to a knee joint, the first axis can be aligned with the epicondyles of the distal femur. The method further includes the step of balancing the weight of the second frame with a counterweight about the first axis, e.g., such as with a first counterweight 40 described in the above embodiment. Then, applying a force to the joint and then measuring displacement of the second body segment relative to the first body segment upon application of the force. The displacement of the second body segment relative to the first body segment upon application of the force is determined by measuring displacement of the second frame relative to the first frame.

Exemplary Application of the Apparatus

Individuals between 1.5 and 2.0 meters tall with a BMI between 18 and 25 can be assessed for 3D knee joint stability. Subjects will be seated in an adjustable chair and the knee affixed to the apparatus of the present invention. Motions of the tibia will be measured relative to the fixed femur in response to combined valgus and internal rotation torques of 8 Nm and 4 Nm, respectively. Loads will be applied to the knee at a slow, constant rate while the subject maintains a relaxed state. Tests will be conducted with the knee flexed to 5°, 15°, and 30°, since these angles typically elicit the largest coupled A/P displacements. Three loading cycles will be applied. Since notable variation between the first and subsequent cycles occurs, only motions from cycles two and three will be averaged and analyzed. The applied torques mimics a clinical exam, which generates ≤100N in the anterior cruciate ligament (ACL).

The continuous load displacement response of the knee to the multiplanar torques will be visualized and recorded using custom software. Recording continuous data allows us to assess reliability of each output displacement over the entire range of applied torques in each degree of freedom. One limb of each subject can be assessed at random by two physical therapists on two occasions. Mean and standard deviation (s.d.) of each output displacement at load increments of 0.5 Nm for each tester and for each repeat test will be calculated. Inter- and intra-operator agreement will be quantified using intraclass correlation coefficients (ICC) as a measure of reliability. Standard error of measurement will be calculated as a measure of precision. Minimal detectable change using a confidence interval of 95% can be calculated to determine the smallest measured difference that exceeds variations due to chance.

The primary outcome measure is the coupled anterior translation that will occur in response to the combined torques because this motion strongly correlates with the pivot shift phenomenon. Secondary outcomes are all other rotations and translations measured by the apparatus. Detection of differences in 3D motions between the ACL-intact and reconstructed knees are expected. Differences of at least 1.5±2.0 mm between these conditions are expected as a primary outcome measure.

From the foregoing description, it can be seen that the present invention comprises an apparatus for determining 3D load displacement response of a joint. It will be appreciated by those skilled in the art that changes could be made to the embodiments described above without departing from the broad inventive concept thereof. It is to be understood, therefore, that this invention is not limited to the particular embodiments disclosed, but it is intended to cover modifications within the spirit and scope of the present invention as defined by the appended claims.

I claim:

1. An apparatus for determining 3D load displacement response of a joint having a first body segment and a second body segment moveable with respect to the first body segment, comprising:
   a first frame for securing the first body segment; and
   a load displacement assembly that includes:
      a first axis for alignment with a first anatomical plane of the joint,
      a second frame for securing the second body segment, the second frame movable relative to the first frame,
      a first counterweight configured to balance a weight of the second frame,
      an actuator for applying a force to the second frame, and
      a sensor for measuring displacement of the second frame relative to the first frame upon application of the force.

2. The apparatus of claim 1, wherein the second frame extends from the first axis and the first counterweight balances the weight of the second frame about the first axis.

3. The apparatus of claim 1, wherein the load displacement assembly further comprises a second counterweight configured to balance the weight of the load displacement assembly about the first axis.

4. The apparatus of claim 1, wherein the load displacement assembly further comprises:
   a second axis for alignment with a second anatomical plane of the joint; and
   a third axis for alignment with a third anatomical plane of the joint.

5. The apparatus of claim 4, wherein the load displacement assembly further comprises a second counterweight that translates along a path substantially parallel to the third axis and balances the weight of the load displacement assembly.

6. The apparatus of claim 4, wherein the load displacement assembly further comprises a third counterweight that balances the weight of the load displacement assembly about the second axis.

7. The apparatus of claim 6, wherein the third counterweight translates along a path substantially parallel to the second axis.

8. The apparatus of claim 4, wherein the load displacement assembly further comprises a fourth counterweight configured to balance the weight of the load displacement assembly about the third axis.

9. The apparatus of claim 4, wherein the force applies a torque to the joint about the second or third axes or a linear force to translate the joint in a direction perpendicular to the first axis.

10. The apparatus of claim 4, wherein the load displacement assembly further comprises:
   a bearing having:
      a stationary part mounted to a shaft extending along the first axis, and
      a moving part connected to the second frame; and
   the actuator applies the force to the moving part to generate a torque about the third axis.

11. The apparatus of claim 1, wherein the load displacement assembly further comprises:
   a linear bearing having:
      a stationary part mounted to a shaft extending along the first axis, and
      a moving part connected to the second frame; and
   the actuator applies the force to the moving part to generate a load on the second frame.

12. The apparatus of claim 1, wherein the load displacement assembly further comprises:
   a shaft extending along the first axis;
   a bearing circumscribing the shaft and having a fastener for rigidly fixating the bearing along a section of the shaft; and
   a support for rotatably supporting the bearing and a fastener for rigidly fixating the bearing on the support.

13. An apparatus for applying loads about multiple axes of a joint without interfering with coupled or primary motions for determining 3D load displacement characteristics of the joint formed by a first body segment and a second body segment moveable with respect to the first body segment, comprising:
   a first frame for securing the first body segment;
   a first axis for alignment with a first anatomical plane of the joint;
   a second axis for alignment with a second anatomical plane of the joint;
   a third axis for alignment with a third anatomical plane of the joint;
   a weightless second frame for securing the second body segment, the second frame movable relative to the first frame and extending from the first axis;
   a first actuator for applying a first force to the joint;
   a second actuator for applying a second force independent of the first force to the joint; and
   a first displacement sensor for measuring displacement of the second frame relative to the first frame upon application of at least one of the first and second forces.

14. The apparatus of claim 13, wherein the first displacement sensor measures displacement upon application of the first force, and further comprising a second displacement sensor for measuring displacement of the second frame relative to the first frame upon application of the second force.

15. The apparatus of claim 14, wherein the first and second forces are applied simultaneously and the first and second displacement sensors measure displacement simultaneously.

16. The apparatus of claim 13, further comprising a third force independent of the first and second forces for applying a third load to the joint.

17. The apparatus of claim 13, further comprising:
   a weightless linear bearing having:
      a stationary part mounted to a shaft extending along the first axis, and
      a moving part connected to the second frame.

18. The apparatus of claim 13, further comprising:
   a weightless rotational bearing having:
      a stationary part mounted to a shaft extending along the first axis, and
      a moving part connected to the second frame.

19. A method of objectively assessing the 3D load displacement response of a joint formed by a first body segment and a second body segment comprising:
   securing the first body segment to a stationary first frame;
   securing the second body segment to a second frame of a load displacement assembly, wherein the second frame is movable relative to the first frame about a first axis;
   balancing the weight of the second frame with a counterweight about the first axis;
   applying a force to the joint; and
   measuring displacement of the second body segment relative to the first body segment upon application of the force.

20. The method of claim 19, wherein the measuring step, the displacement of the second body segment relative to the first body segment upon application of the force is determined by measuring displacement of the second frame relative to the first frame.

21. An apparatus for determining 3D load displacement response of a joint having a first body segment and a second body segment moveable with respect to the first body segment, comprising:
   a first frame for securing the first body segment; and
   a load displacement assembly that includes:
      a first axis for alignment with a first anatomical plane of the joint,
      a second frame for securing the second body segment, the second frame movable relative to the first frame,
      a first counterweight balancing a weight of the second frame,
      a bearing having:
         a stationary part mounted to a shaft extending along the first axis, and
         a moving part connected to the second frame,
      an actuator for applying a force to the moving part, and
      a sensor for measuring displacement of the second frame relative to the first frame upon application of the force.

22. An apparatus for applying loads about multiple axes of a joint formed by a first body segment and a second body segment moveable with respect to the first body segment, comprising:
   a first frame for securing the first body segment;
   a first axis for alignment with a first anatomical plane of the joint;
   a second axis for alignment with a second anatomical plane of the joint;

a third axis for alignment with a third anatomical plane of the joint;
a weightless second frame for securing the second body segment, the second frame movable relative to the first frame and extending from the first axis;
a weightless linear bearing having:
   a stationary part mounted to a shaft extending along the first axis, and
   a moving part connected to the second frame;
a first actuator for applying a first force to the moving part of the second frame;
a second actuator for applying a second force independent of the first force to the joint; and
a displacement sensor for measuring displacement of the second frame relative to the first frame upon application of at least one of the first and second forces.

* * * * *

UNITED STATES PATENT AND TRADEMARK OFFICE
CERTIFICATE OF CORRECTION

PATENT NO. : 9,566,022 B2  
APPLICATION NO. : 14/209538  
DATED : February 14, 2017  
INVENTOR(S) : Carl Imhauser, Brendan Dugan and Jeffrey Kinsberg Page 1 of 1

It is certified that error appears in the above-identified patent and that said Letters Patent is hereby corrected as shown below:

On the Title Page

Item (72) reading:
"Carl Imhauser, South Orange, NJ (US)"
Should read:
--Carl Imhauser, South Orange, NJ (US); Brendan Dugan, Weatogue, CT (US); Jeffrey Kinsberg, Clarksburg, NJ (US)--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*